US007321057B2

United States Patent
Hirata et al.

(10) Patent No.: US 7,321,057 B2
(45) Date of Patent: Jan. 22, 2008

(54) METHOD FOR MANUFACTURING PROSTAGLANDIN ANALOGUE

(75) Inventors: Ryu Hirata, Sanda (JP); Tatsuya Matsukawa, Kobe (JP)

(73) Assignee: R-Tech Ueno, Ltd., Tokyo (JP)

( * ) Notice: Subject to any disclaimer, the term of this patent is extended or adjusted under 35 U.S.C. 154(b) by 0 days.

(21) Appl. No.: 11/193,373

(22) Filed: Aug. 1, 2005

(65) Prior Publication Data

US 2006/0036108 A1 Feb. 16, 2006

Related U.S. Application Data

(60) Provisional application No. 60/592,398, filed on Aug. 2, 2004.

(51) Int. Cl.
*C07C 61/06* (2006.01)
*C07C 49/00* (2006.01)
*C07C 35/06* (2006.01)

(52) U.S. Cl. .................. 562/503; 568/379; 568/838
(58) Field of Classification Search ............... 560/121; 562/503, 504; 568/338, 343, 346, 351, 354, 568/379, 838
See application file for complete search history.

(56) References Cited

U.S. PATENT DOCUMENTS

| 5,073,569 A | 12/1991 | Ueno et al. |
| 5,166,174 A | 11/1992 | Ueno et al. |
| 5,212,324 A | 5/1993 | Ueno |
| 5,221,763 A | 6/1993 | Ueno et al. |
| 5,739,161 A | 4/1998 | Ueno |
| 6,242,485 B1 | 6/2001 | Ueno |

OTHER PUBLICATIONS

Bulletin of the Chemical Society of Japan (2004), 77(9), 1745-1755, CAS online [retrieved May 23, 2007] from STN, Columbus, OH, USA.*
Chemical Safety, 2-Iodoxybenzoic Acid; J.B.Plumb, D. J. Harper; Chem Eng. News, Jul. 16, 1990 p. 3.

* cited by examiner

*Primary Examiner*—Karl Puttlitz
(74) *Attorney, Agent, or Firm*—Sughrue Mion, PLLC

(57) ABSTRACT

The present invention provides a new method for manufacturing a prostaglandin analogue having one or more keto groups on the 5-membered ring and/or omega chain, which comprises the step of treating a corresponding hydroxyl group containing compound with a co-oxidizer under the presence of a tetramethylpyperidine-1-oxyl derivative to form the desired prostaglandin analogue. The method of the invention can be carried out easily under relatively mild conditions.

3 Claims, No Drawings

METHOD FOR MANUFACTURING PROSTAGLANDIN ANALOGUE

CROSS-REFERENCE TO RELATED PATENT APPLICATION

This application claims the benefit of U.S. Provisional Application No. 60/592,398, filed on Aug. 2, 2004, in the U.S. Patent and Trademark Office, the disclosure of which is incorporated herein in its entirety by reference.

BACKGROUND OF THE INVENTION

1. Field of the invention

The present application relates to a novel method for manufacturing a prostaglandin analogue which is used for active ingredients of pharmaceuticals.

2. Art Related

Oxidation of hydroxyl group is an important reaction step to produce a prostaglandin analogue having keto group on the 5-membered ring and/or the omega chain of its prostanoic acid skeleton.

Swern oxidation that has been conventionally used for prostaglandin syntheses requires manufacturing equipment that can operate at a very low reaction temperature (−70 to −40C.). In addition, when the prostaglandin analogue has a carboxyl group in the molecular, protection of the carboxyl group is needed before Swern oxidation.

Traditional oxidation using heavy metal reagents such as chromic acid can be used for oxidation of compounds having carboxyl group. However, most of heavy metals are toxic and occasionally not suitable as industrial production methods for pharmaceuticals.

Although Dess-Martin oxidation also can, be used to oxidize compounds having carboxyl group, the heat- and shock-sensitivity of this oxidizing reagent is published (Chem Eng. News, Jul. 16, 3, 1990, the cited reference is incorporated into the present application by reference). In addition, this oxidizing reagent is not easily available as an industrial raw material from the market.

SUMMARY OF THE INVENTION

An object of the present invention is to provide a new method for manufacturing a prostaglandin analogue having one or more keto groups on the 5-membered ring and/or the omega chain, which can be carried out easily under relatively mild conditions.

The present invention provides a method for manufacturing a prostaglandin analogue represented by formula (I):

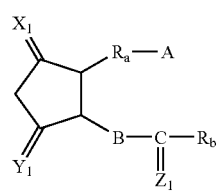

(I)

wherein $X_1$ is

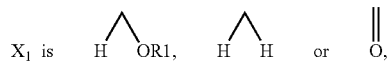

wherein R1 is a protecting group for hydroxy group; $Y_1$ is

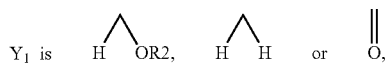

wherein R2 is a protecting group for hydroxy group; $Z_1$ is

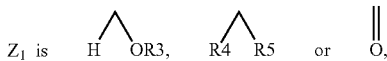

wherein R3 is a protecting group for hydroxy group, R4 and R5 are hydrogen atom, halogen atom, lower alkyl or lower alkoxy group or when R4 and R5 are lower alkyl at the same time, R4 and R5 taken together may form a cyclic group, provided that at least one of $X_1$, $Y_1$ and $Z_1$ is =O;

A is —$CH_3$, —$CH_2OH$, —$COCH_2OH$, —COOH or a functional derivative thereof;

B is a single bond, —$CH_2$—, —$CH_2$—$CH_2$—, —CH=CH- or -C≡C-, —$CH_2$—$CH_2$—$CH_2$—, —CH=CH—$CH_2$—, —$CH_2$—CH=CH—, —C≡C—$CH_2$—or—$CH_2$—C≡C—;

Ra is bivalent saturated or unsaturated lower-medium aliphatic hydrocarbon group, which is unsubstituted or substituted by halogen atom, alkyl, hydroxy, oxo, aryl or heterocyclic group, provided that one or more carbon atoms of the aliphatic hydrocarbon group may optionally be replaced with oxygen, nitrogen or sulfur atom; and Rb is hydrogen atom; saturated or unsaturated lower-medium aliphatic hydrocarbon group which may be substituted by halogen, oxo, hydroxy, lower alkoxy, lower alkanoyloxy, cyclo(lower)alkyl, cyclo(lower)alkyloxy, aryl, aryloxy, heterocyclic or heterocyclic oxy; cyclo(lower)alkyl; cyclo(lower)alkyloxy; aryl; aryloxy; heterocyclic; or heterocyclic oxy, which comprises the step of, reacting a compound of formula (II):

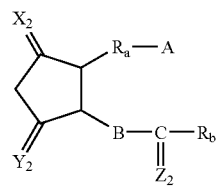

(II)

wherein, $X_2$ is the same as $X_1$ except for when

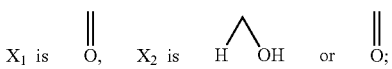

$Y_2$ is the same as $Y_1$ except for when

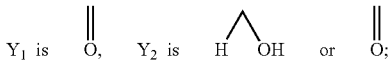

$Z_2$ is the same as $Z_1$ except for when

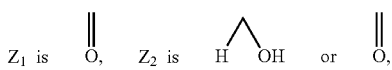

provided that at least one of

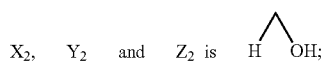

and,

A, B, Ra and Rb are the same as above;
with a co-oxidizer under the presence of a tetramethylpyperidine-1-oxyl derivative.

The compound of formula (I) can be used for manufacturing pharmaceuticals. (see, for example, U.S. Pat. Nos. 5,073,569, 5,166,174, 5,221,763, 5,212,324, 5,739,161 and 6,242,485 (the cited references are herein incorporated by reference)

DETAILED DESCRIPTION OF THE INVENTION

In the definition of above formulae, the term "unsaturated" in the definitions for Ra and Rb is intended to include at least one or more double bonds and/or triple bonds that are isolatedly, separately or serially present between carbon atoms of the main and/or side chains.

The term "lower-medium aliphatic hydrocarbon" means a hydrocarbon having a straight or branched chain of 1 to 14 carbon atoms, wherein the side chain has preferably 1 to 3 carbon atoms. The preferred Ra has 1 to 10, more preferably, 6 to 10 carbon atoms, and the preferred Rb has 1 to 10, more preferably, 1 to 8 carbon atoms.

The term "halogen" includes fluorine, chlorine, bromine, and iodine atoms.

The term "lower" means a group having 1 to 6 carbon atoms unless otherwise specified.

The term "lower alkyl" means a straight- or branched-chain saturated hydrocarbon group having 1 to 6 carbon atoms, for example, methyl, ethyl, propyl, isopropyl, butyl, isobutyl, t-butyl, pentyl, and hexyl.

The term "lower alkoxy" means a lower alkyl-O— wherein the lower alkyl is as described above.

The term "lower alkanoyloxy" means a group represented by the formula RCO—O—, wherein RCO— is an acyl formed by oxidation of a lower alkyl as described above, for example, acetyl.

The term "lower cycloalkyl" means a group formed by cyclization of a lower alkyl group containing 3 or more carbon atoms as described above, for example, cyclopropyl, cyclobutyl, cyclopentyl, and cyclohexyl.

The term "cyclo(lower)alkyloxy" means a group represented by the formula cycloalkyl-O—, wherein cycloalkyl is described above.

The term "aryl" includes aromatic hydrocarbon rings (preferably monocyclic groups), which may be substituted, for example, phenyl, tolyl and xylyl. Examples of the substituents in this case include halogen, and halogen substituted lower alkyl group, wherein halogen atom and lower alkyl group are as described above.

The term "aryloxy" means a group represented by the formula ArO—, wherein Ar is an aryl group as described above.

The term "heterocyclic" includes mono- to tri-cyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen, oxygen and sulfur atoms. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolonyl, benzothiazolyl, phenothiazinyl. Examples of the substituent in this case include halogen, and halogen substituted lower alkyl group, wherein halogen atom and lower alkyl group are as described above.

The term "heterocyclic-oxy" means a group represented by the formula HcO—, wherein Hc is a heterocyclic group as described above.

The term "functional derivative" of A includes salts, preferably pharmaceutically acceptable salts, ethers, esters, and amides.

Examples of suitable "pharmaceutically acceptable salts" include nontoxic salts which are commonly used, and salts with inorganic bases, for example, alkali metal salts (sodium salt, potassium salt and the like); alkaline earth metal salts (calcium salt, magnesium salt and the like); ammonium salts; salts with organic bases, for example, amine salts (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, lysine salt, procaine salt, and caffeine salt); basic amino acid salts (such as arginine salt, and lysine salt); tetraalkyl ammonium salts and the like. These salts may be manufactured from, for example, corresponding acids and bases in accordance with a conventional manner or salt exchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester, and 1-cyclopropylethyl ester; lower alkenyl esters such as vinyl ester, and allyl ester; lower alkynyl esters such as ethynyl ester, and propynyl ester; hydroxy(lower)alkyl esters such as hydroxyethyl ester; and lower alkoxy(lower)alkyl esters such as methoxymethyl ester, and 1-methoxyethyl ester as well as, for example, optionally substituted aryl esters such as phenyl ester, tosyl ester, t-butylphenyl ester, salicyl ester, 3,4-dimethoxyphenyl ester, and benzamidephenyl ester; and aryl(lower)alkyl esters such as benzyl ester, trityl ester, and benzhydryl ester.

An amide for A is a group represented by formula: —CONR'R", wherein R' and R" independently represent hydrogen atom, lower alkyl, aryl, alkyl- or aryl-sulfonyl, lower alkenyl or lower alkynyl. Examples of amides include mono- or di-lower alkyl amides such as methylamide, ethylamide, and dimethylamide; aryl amides such as anilide, and toluidide; and alkyl- or aryl-sulfonyl amides such as methylsulfonyl amide, ethylsulfonyl amide, and tolylsulfonyl amide.

Preferred examples of A include —COOH, and a pharmaceutically acceptable salt, an ester and an amide thereof.

Preferred B is —$CH_2$—$CH_2$— which provides the structure of so-called, 13,14-dihydro type prostaglandin derivative.

Preferred Ra is a hydrocarbon having 1-10 carbon atoms, more preferably, 6-10 carbon atoms. One or more carbon atom of the hydrocarbon group may optionally be replaced with oxygen, nitrogen or sulfur atom.

Examples of Ra include, for example, the following groups:

—$CH_2$—$CH_2$—$CH_2$—$CH_2$—$CH_2$—$CH_2$—,

—$CH_2$—CH=CH—$CH_2$—$CH_2$—$CH_2$—,

—$CH_2$—$CH_2$—$CH_2$—$CH_2$—CH=CH—,

—$CH_2$—C≡C—$CH_2$—$CH_2$—$CH_2$—,

—$CH_2$—$CH_2$—$CH_2$—$CH_2$—CH($CH_3$)—$CH_2$—,

—$CH_2$—$CH_2$—$CH_2$—$CH_2$—O—$CH_2$—,

—$CH_2$—CH=CH—$CH_2$—O—$CH_2$—,

—$CH_2$—C≡C—$CH_2$—O—$CH_2$—,

—$CH_2$—$CH_2$—$CH_2$—$CH_2$—$CH_2$—$CH_2$—$CH_2$—,

—$CH_2$—CH=CH—$CH_2$—$CH_2$—$CH_2$—$CH_2$—,

—$CH_2$—$CH_2$—$CH_2$—$CH_2$—$CH_2$—CH=CH—,

—$CH_2$—C≡C—$CH_2$—$CH_2$—$CH_2$—$CH_2$—,

—$CH_2$—$CH_2$—$CH_2$—$CH_2$—$CH_2$—CH($CH_3$)—$CH_2$—,

—$CH_2$—$CH_2$—$CH_2$—$CH_2$—$CH_2$—$CH_2$—$CH_2$—$CH_2$—,

—$CH_2$—CH=CH—$CH_2$—$CH_2$—$CH_2$—$CH_2$—$CH_2$—,

—$CH_2$—$CH_2$—$CH_2$—$CH_2$—$CH_2$—$CH_2$—CH=CH—,

—$CH_2$—C≡C—$CH_2$—$CH_2$—$CH_2$—$CH_2$—$CH_2$—,

—$CH_2$—$CH_2$—$CH_2$—$CH_2$—$CH_2$—$CH_2$—CH($CH_3$)—$CH_2$—,

Preferred Rb is hydrogen atom or a hydrocarbon containing 1-10 carbon atoms, more preferably, 1-8 carbon atoms and, which may be substituted by halogen atom such as fluorine.

In the specification and claims, the term "a protecting group for hydroxy" means a functional group which is introduced to protect the hydroxy group from oxidization. In the present invention, the protecting group may be any group as long as it can act as such. Examples of the protecting groups may include methyl, methoxymethyl, ethyl, 1-ethoxyethyl, benzyl, substituted benzyl, allyl, tetrapyranyl, t-butyldimethylsilyl, triethylsilyl, triisopropylsilyl, diphenylmethylsilyl, formyl, acetyl, substituted acetyl, benzoyl, substituted benzoyl, methyloxycarbonyl, benzyloxycarbonyl, t-buthloxycarbonyl and allyloxycarbonyl groups.

The compound of formula(II) used in the present invention has been known to the art and may be obtained by any known means for preparing prostaglandin analogues. For example, U.S. Pat. Nos. 5,073,569, 5,166,174, 5,221,763, 5,212,324, 5,739,161 and 6,242,485(the cited references are herein incorporated by reference) disclose a compound of formula (II) having an OH— group and a method for preparing the same as an intermediate or an objective substance.

Examples of the tetramethylpiperidine-1-oxyl derivative used in the present invention may include 2,2,6,6,-tetramethylpiperidine-1-oxyl (TEMPO), 4-hydroxy-2,2,6,6,-tetramethylpiperidine-1-oxyl, 4-amino-2,2,6,6,-tetramethylpiperidine-1-oxyl, 4-oxo-2,2,6,6,-tetramethylpiperidine-1-oxyl, 4-methoxy-2,2,6,6,-tetramethylpiperidine-1-oxyl, 4-acetoamide 2,2,6,6,-tetramethylpiperidine-1-oxyl, 4-carboxy-2,2,6,6,-tetramethylpiperidine-1-oxyl, 4-cyano 2,2,6,6,-tetramethylpiperidine-1-oxyl and 4-acetylamino 2,2,6,6,-tetramethylpiperidine-1-oxyl.

The amount of the tetramethylpiperidine-1-oxyl derivative used in the reaction may be about 0.001-5.0 mole, preferably about 0.001-0.2 mole per one molar equivalent of the hydroxyl group of the starting compound to be oxidized or a compound of formula (II).

The co-oxidizer used in the present invention may be any as long as it can convert the tetramethylpiperidine-1-oxyl derivative into the active form. Examples of co-oxidizers may include hypohalogenous acid such as hypochlorous acid or a salt thereof, halogenous acid such as bromous acid or a salt thereof, compounds having polyvalent iodine such as iodobenzene acetate, peroxides such as 3-chloro-perbenzoidc acid, N-halogen substituted succinimides such as N-chloro succinimide.

The amount of the co-oxidizer in the reaction may be 1.1-3 molar equivalents, preferably 1.1-2 molar equivalents and more preferably 1.1-1.5 molar equivalent per one molar equivalent of the hydroxy group to be oxidized.

The reaction may be conducted in an organic solvent, an aqueous solvent, a mixture thereof, or a two-phase solvent system consisting of an organic and an aqueous solvents.

Examples of organic solvents used in the present invention may be aromatic hydrocarbon solvent such as toluene, aliphatic hydrocarbon solvent such as hexane, halogen containing solvent such as dichloromethane, ketones such as acetone, esters such as ethyl acetate.

The aqueous solvent may contain a pH adjusting agent such as sodiumhydrogen carbonate, pH buffering such as potassium dihydrogen phosphate and sodium dihydrogen phosphate.

According to the present invention, a halogenated salt such as sodium bromide, potassium bromide, tetrabutylammonium bromide, and tetrabuthlammonium chloride may be added to the reaction in order to facilitate the reaction. The amount of the halogenated salt to be added is not limited and may be about 1.0-2.0 molar equivalents per one molar equivalent of the hydroxyl group to be oxidized.

In the present invention, the alcohol compound of formula (II) is reacted with the co-oxidizer under the presence of the tetramethylpiperidine-1-oxyl derivative. According to the present invention, the reaction may be carried out at a temperature of −10 to 50° C., preferably, about 0 to 20° C.

The present invention will be illustrated in more detail by way of the following examples. These examples should not be used as any limitation of the present invention.

EXAMPLE 1

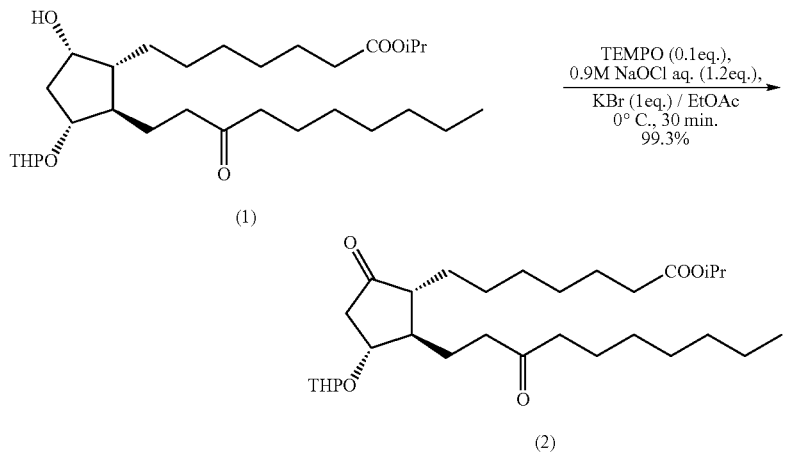

An alcohol compound (1) 0.102 g (0.20 mmol) was dissolved in ethyl acetate 0.69 ml, and TEMPO in ethyl acetate 0.313 ml (10 mg/ml, 0.02 mmol) was added thereto. The mixture was cooled to 0° C. Three percent aqueous sodium hydrogen carbonate 0.56 ml (0.2 mmol) and potassium bromide 23.8 mg (0.20 mmol) were added thereto. About 0.9M aqueous sodium hypochlorite 0.27 ml (0.24 mmol) was added dropwise to the reaction, and the mixture was stirred for 30 minutes at 0° C. and added with saturated aqueous sodium thiosulfate. Then, the reaction mixture was extracted three times with ethyl acetate. The extract was washed with dilute hydrochloric acid, saturated aqueous sodium hydrogen carbonate and brine, dried with anhydrous magnesium sulfate, filtered and concentrated under vacuum. The residue was purified with silica gel flash chromatography (column: BW-300 60 g, ethyl acetate-hexane 30:70) to give the desired compound (2) as colourless-oil. Yield 0.101 g (99.3%).

$^1$H NMR (200 MHz in CDCl$_3$, TMS=0 ppm) δ 0.88 (3H, t, J=6.5 Hz) 1.24 (6H, t, J=6.5 Hz) 1.20-2.80 (36H, m) 2.25 (2H, t, J=7.6 Hz) 3.41-3.60 (1H, m) 3.74-3.98 (1.5H, m) 4.14 (0.5H, q, J=7.0 Hz) 4.54-4.60 (0.5H, m) 4.64-4.71 (0.5H, m) 5.00 (1H, septet, J=6.2 Hz)

EXAMPLE 2

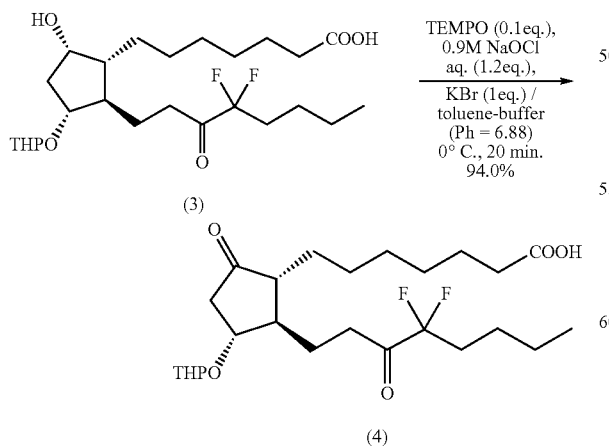

An alcohol compound (3) 0.172 g (0.361 mmol) was dissolved in toluene 1.25 ml, potassium bromide 43 mg (0.36 mmol) was added thereto and the mixture was cooled to 0° C. Neutral phosphate buffer 3.6 ml and TEMPO in toluene 0.56 ml (10 mg/ml, 0.0361 mmol) were added thereto. About 0.9M aqueous sodium hypochlorite 0.48 ml (0.433 mmol) was added dropwise to the reaction, and the mixture was stirred for 20 minutes at 0° C. Saturated aqueous sodium thiosulfate and 1N hydrochloric acid 0.36 ml were added to the reaction. Then, the reaction mixture was extracted three times with ethyl acetate. The extract was washed with water and dilute hydrochloric acid, dried with anhydrous magnesium sulfate, filtered and concentrated under vacuum. The residue was purified with silicagel column (column: FL-60D, 36 g) to give the desired compound (4) as colourless oil. Yield 0.161 g (94.0%).

$^1$H NMR (200 MHz in CDCl$_3$, TMS=0 ppm) δ 0.92 (3H, t, J=7.0 Hz) 1.11-2.45 (29H, m) 2.34 (2H, t, J=7.3 Hz) 2.65-3.11 (3H, m) 3.42-3.60 (1H, m) 3.75-3.97 (1.5H, m) 4.16 (0.5H, q, J=7.3 Hz) 4.54-4.65 (0.5H, m) 4.65-4.74 (0.5H, m)

EXAMPLE 3

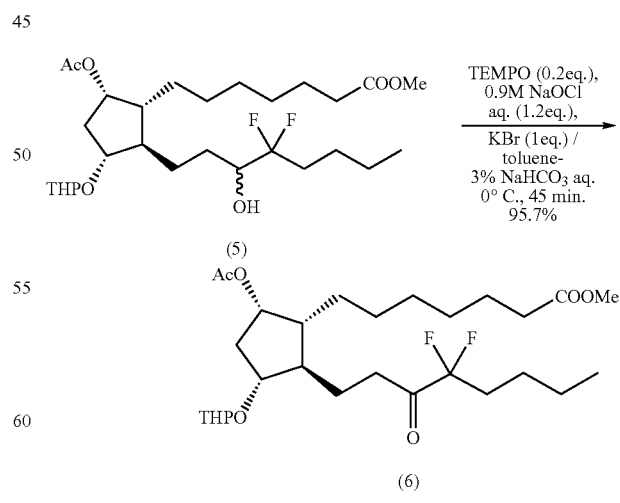

An alcohol compound (5) 0.107 g (0.20 mmol) was dissolved in toluene 0.38 ml, and TEMPO in toluene 0.62 ml (10 mg/ml, 0.04 mmol) was added thereto. The mixture was cooled to 0° C. Three percent aqueous sodium hydrogen carbonate 0.56 ml(0.2 mmol) and potassium bromide 23.8 mg (0.20 mmol) were added thereto. About 0.9M aqueous sodium hypochlorite 0.27 ml (0.24 mmol) was added dropwise to the reaction, and the mixture was stirred for 45 minutes at 0° C. After that, the reaction mixture was added with saturated aqueous sodium thiosulfate and then, extracted three times with ethyl acetate. The extract was washed with dilute hydrochloric acid, saturated aqueous sodium hydrogen carbonate and brine, dried with anhydrous magnesium sulfate, filtered and concentrated under vacuum. The residue was purified with silica gel flash chromatography (column: BW-300 70 g, ethyl acetate-hexane 25:75) to give the desired compound (6) as colourless oil. Yield 0.102 g (95.7%).

$^1$H NMR (200 MHz in CDCl$_3$, TMS=0 ppm) δ 0.92 (3H, t, J=7.1 Hz) 1.11-2.13 (26H, m) 2.03 (3H, s) 2.30 (2H, t, J=7.4 Hz) 2.13-2.44 (3H, m) 2.73-3.15 (3H, m) 3.40-3.55 (1H, m) 3.62-4.00 (2H, m) 3.67 (3H, s) 4.47-4.60 (1H, m) 5.01-5.13 (1H, m)

EXAMPLE 4

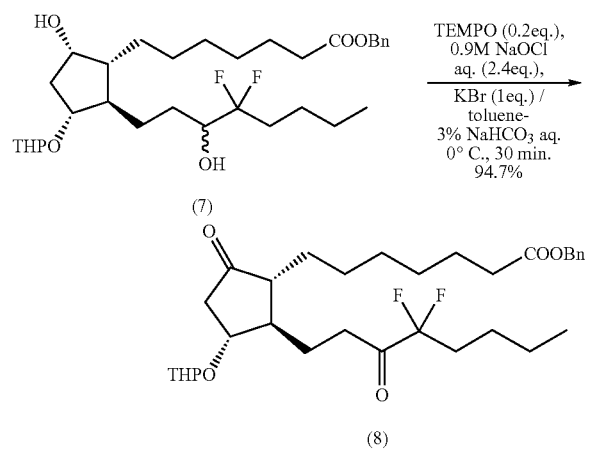

An alcohol compound (7) 0.114 g (0.20 mmol) was dissolved in toluene 0.38 ml, and TEMPO in toluene 0.62 ml (10 mg/ml, 0.04 mmol) was added thereto. The mixture was cooled to 0° C. Three percent aqueous sodium hydrogen carbonate 1.12 ml (0.4 mmol) and potassium bromide 48 mg (0.40 mmol) were added thereto. About 0.9M aqueous sodium hypochlorite 0.54 ml (0.48 mmol) was added dropwise to the reaction, and the mixture was stirred for 30 minutes at 0° C. After that, the reaction mixture was added with saturated aqueous sodium thiosulfate and then, extracted three times with ethyl acetate. The extract was washed with dilute hydrochloric acid, saturated aqueous sodium hydrogen carbonate and brine, dried with anhydrous magnesium sulfate, filtered and concentrated under vacuum. The residue was purified with silica gel flash chromatography (column: BW-300 70 g, ethyl acetate-hexane 30:70) to give the desired compound (8) as colourless oil. Yield 0.107 g (94.7%).

$^1$H NMR (200 MHz in CDCl$_3$, TMS=0 ppm) δ 0.92 (3H, t, J=7.1 Hz) 1.14-2.45 (27H, m) 2.35 (2H, t, J=7.5 Hz) 2.62-3.10 (3H, m) 3.43-3.60 (1H, m) 3.74-3.95 (1.5H, m) 4.15 (0.5H, q, J=7.5 Hz) 4.54-4.63 (0.5H, m) 4.63-4.72 (0.5H, m) 5.11 (2H, s) 7.29-7.43 (5H, m)

EXAMPLE 5

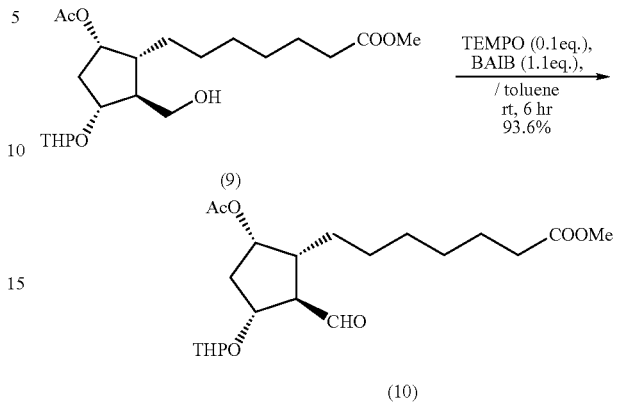

An alcohol compound (9) 0.204 g (0.509 mmol) was dissolved in dichloromethane anhydrous 15 ml, and TEMPO in toluene 0.796 ml (10 mg/ml, 0.0509 mmol) was added thereto. Solid [bis(acetoxy)iodo]benzene (BAIB) 0.180 g (0.560 mmol) was added to the mixture and the mixture was stirred for 6 hours at room temperature. After that, saturated aqueous sodium thiosulfate was added to the reaction and the reaction mixture was extracted three times with ethyl acetate. The extract was washed with dilute hydrochloric acid, saturated aqueous sodium hydrogen carbonate and brine, dried with anhydrous magnesium sulfate, filtered and concentrated under vacuum. The residue was purified with silica gel flash chromatography (column: BW-300 80 g, ethyl acetate-hexane 20:80) to give the desired compound (10) as colourless oil. Yield 0.190 g (93.6%).

$^1$H NMR (200 MHz in CDCl$_3$, TMS=0 ppm) δ 1.10-2.48 (19H, m) 2.07 (3H, s) 2.29 (2H, t, J=7.42 Hz) 2.76-3.07 (1H, m) 3.36-3.56 (1H, m) 3.66 (3H, s) 3.74-3.88 (1H, m) 4.31-4.50 (1H, m) 4.50-4.63 (1H, m) 5.08-5.21 (1H, m) 9.78 (1H, dd, J=3.0, 10.2 Hz)

COMPARATIVE EXAMPLE 1

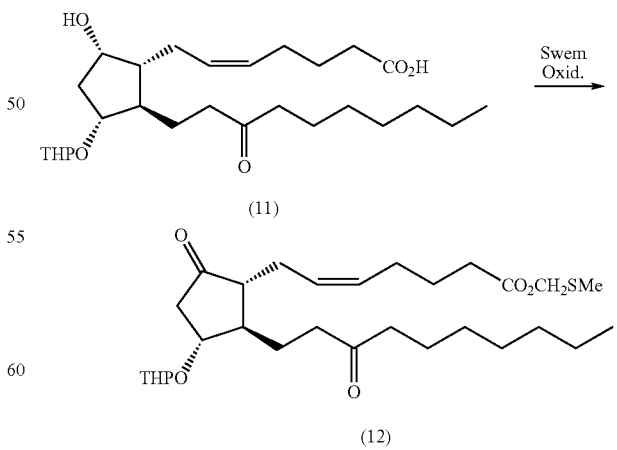

Oxalyl chloride 0.61 ml (6.99 mmol) was dissolved in dichloromethane 7 ml and the solution was cooled to −78° C. DMSO 0.99 ml (13.98 mmol) was added slowly dropwise thereto and the mixture was stirred for 10 minutes. The alcohol compound (11) 1.05 g (2.33 mmol) in dichloromethane was added dropwise thereto and the reaction mixture was stirred for 1 hour. After that, triethylamine 2.03 ml (14.56 mmol) was added dropwise to the reaction and stirred for further 1 hour at 0° C. Then, water was added to the reaction and the reaction mixture was extracted with dichloromethane. The extract was washed with brine, dried with anhydrous magnesium sulfate, filtered and concentrated under vacuum. The residue was purified with silica gel flash chromatography (column: Merck 7734 40 g, ethyl acetate-hexane 20:80) to give the desired methylthioester (12). Yield 1.15 g (94.0%)

$^1$H NMR (200 MHz in CDCl3, TMS=0 ppm) δ0.88 (3H, t, J=6.8 Hz) 1.27 (6H, bs) 2.24 (3H, s) 1.45-2.82 (27H, m) 3.43-3.59 (1H, m) 3.74-3.90 (1H, m) 3.92 (0.5H, q, J=6.8 Hz) 4.16 (0.5H, q, J=6.8 Hz) 4.57 (0.5H, bs) 4.67 (0.5H,bs) 5.13 (3H, s) 5.28-5.54 (2H, m)

What is claimed is:

1. A method for manufacturing a prostaglandin analogue represented by formula (I):

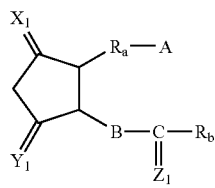

wherein $X_1$ is 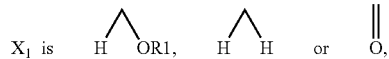

wherein R1 is a protecting group for hydroxy group;

$Y_1$ is 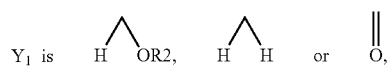

wherein R2 is a protecting group for hydroxy group;

$Z_1$ is 

wherein R3 is a protecting group for hydroxy group, R4 and R5 are hydrogen atom, halogen atom, lower alkyl or lower alkoxy group or when R4 and R5 are lower alkyl at the same time, R4 and R5 taken together may form a cyclic group, provided that at least one of

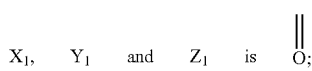

A is

or a functional derivative thereof;

B is a single bond,

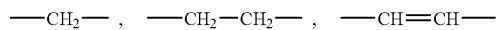
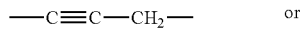
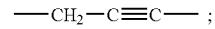

Ra is bivalent saturated or unsaturated lower-medium aliphatic hydrocarbon group, which is unsubstituted or substituted by a halogen atom, an alkyl, hydroxy, oxo, aryl or heterocyclic group, provided that one or more carbon atoms of the aliphatic hydrocarbon group may optionally be replaced with oxygen, nitrogen or sulfur atom; and Rb is hydrogen atom; saturated or unsaturated lower-medium aliphatic hydrocarbon group which may be substituted by a halogen, oxo, hydroxy, lower alkoxy, lower alkanoyloxy, cyclo(lower)alkyl, cyclo(lower)alkyloxy, aryl, aryloxy, heterocyclic or heterocyclic oxy; cyclo(lower)alkyl; cyclo(lower)alkyloxy; aryl; aryloxy; heterocyclic; or heterocyclic oxy, which comprises the step of, reacting a compound of formula (II):

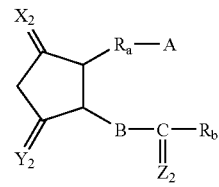

wherein, $X_2$ is the same as $X_1$ except for when

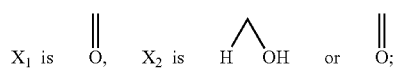

$Y_2$ is the same as $Y_1$ except for when

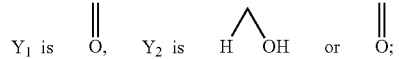

$Z_2$ is the same as $Z_1$ except for when

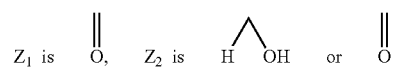

provided that at least one of

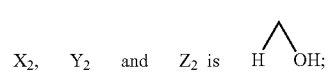

and,
A, B, Ra and Rb are the same as above;
with a co-oxidizer in the presence of a tetramethylpiperidine-1-oxyl derivative;
wherein at least one of $X_2$, $Y_2$, and $Z_2$ that is $H\text{-}OH$ becomes $=O$ as a result of the reacting step.

2. The method of claim 1, wherein A is

—COOH or a functional derivative thereof.

3. The method of claim 1, wherein the tetramethylpiperidine-1-oxyl derivative is 2, 2, 6, 6-tetramethylpiperidine-1-oxyl.

* * * * *

UNITED STATES PATENT AND TRADEMARK OFFICE
Certificate

Patent No. 7,321,057 B2                                              Patented: January 22, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Ryu Hirata, Sanda (JP); Tatsuya Matsukawa, Kobe (JP); and Ryuji Ueno, Potomac, MD (US).

Signed and Sealed this Twenty-third day of October 2012.

*JOHANN R. RICHTER*
*Supervisory Patent Examiner*
Art Unit 1621
Technology Center 1600